United States Patent [19]

Schwabe et al.

[11] Patent Number: 5,486,767
[45] Date of Patent: Jan. 23, 1996

[54] METHOD AND SYSTEM FOR DETECTING DEFECTS IN PIPES OR OTHER STRUCTURES

[75] Inventors: Robert J. Schwabe, Katonah; Michael R. Eggleston, Scotia; Louis F. Coffin, Jr., Schenectady, all of N.Y.

[73] Assignee: General Electric Company, Schenectady, N.Y.

[21] Appl. No.: 206,297

[22] Filed: Mar. 3, 1994

[51] Int. Cl.[6] .................................................. G01R 27/14
[52] U.S. Cl. ........................ 324/715; 324/718; 324/522
[58] Field of Search .................................. 324/537, 713, 324/715, 718, 719, 756, 722, 522, 754, 515

[56] References Cited

U.S. PATENT DOCUMENTS

| | | | |
|---|---|---|---|
| 2,124,578 | 7/1938 | Knerr et al. | 324/718 |
| 3,611,125 | 10/1971 | Sharon | 324/715 |
| 4,267,506 | 5/1981 | Sheill | 324/719 |
| 4,633,176 | 12/1986 | Reimer | 324/758 |
| 4,656,595 | 4/1987 | Hognestad | 324/718 |
| 4,749,945 | 6/1988 | Bonifert et al. | 324/755 |
| 4,758,777 | 7/1988 | Bossard | 324/724 |
| 4,857,833 | 9/1989 | Gonzalez et al. | 324/522 |
| 4,888,546 | 12/1989 | Berry et al. | 324/715 |
| 4,982,154 | 1/1991 | Schwabe et al. | 324/718 |
| 4,989,154 | 1/1991 | Yamashita et al. | 324/715 |
| 5,004,977 | 4/1991 | Kazama | 324/756 |

FOREIGN PATENT DOCUMENTS

| | | | |
|---|---|---|---|
| 0048768 | 3/1986 | Japan | 324/715 |
| 0014051 | 1/1987 | Japan | 324/715 |
| 0047544 | 3/1987 | Japan | 324/718 |
| 1640622 | 4/1991 | U.S.S.R. | 324/718 |

*Primary Examiner*—Maura K. Regan
*Attorney, Agent, or Firm*—R. Thomas Payne; James Magee, Jr.

[57] ABSTRACT

A method and system for rapidly connecting and rapidly disconnecting a large number of point contacts onto a pipe surface for detecting defects in pipe and other structures is taught. The method and system involve independently pressing a plurality of sharply pointed pin contacts onto the pipe surface by a means, such as a spring. The system comprises a plurality of electrodes each having a plurality of pins, as illustrated seventeen (17) pins, arranged in a pattern. Each of the plurality of pins is held in a conforming opening in the electrode and is urged by springs means, such as a coil spring, against the surface of the structures. Each of the plurality of pins (sixteen (16) current pins and one voltage pin) are individually connected to a power supply and sensing apparatus. This system and method has proved operable for detecting defects in structures, such as pipe.

26 Claims, 10 Drawing Sheets

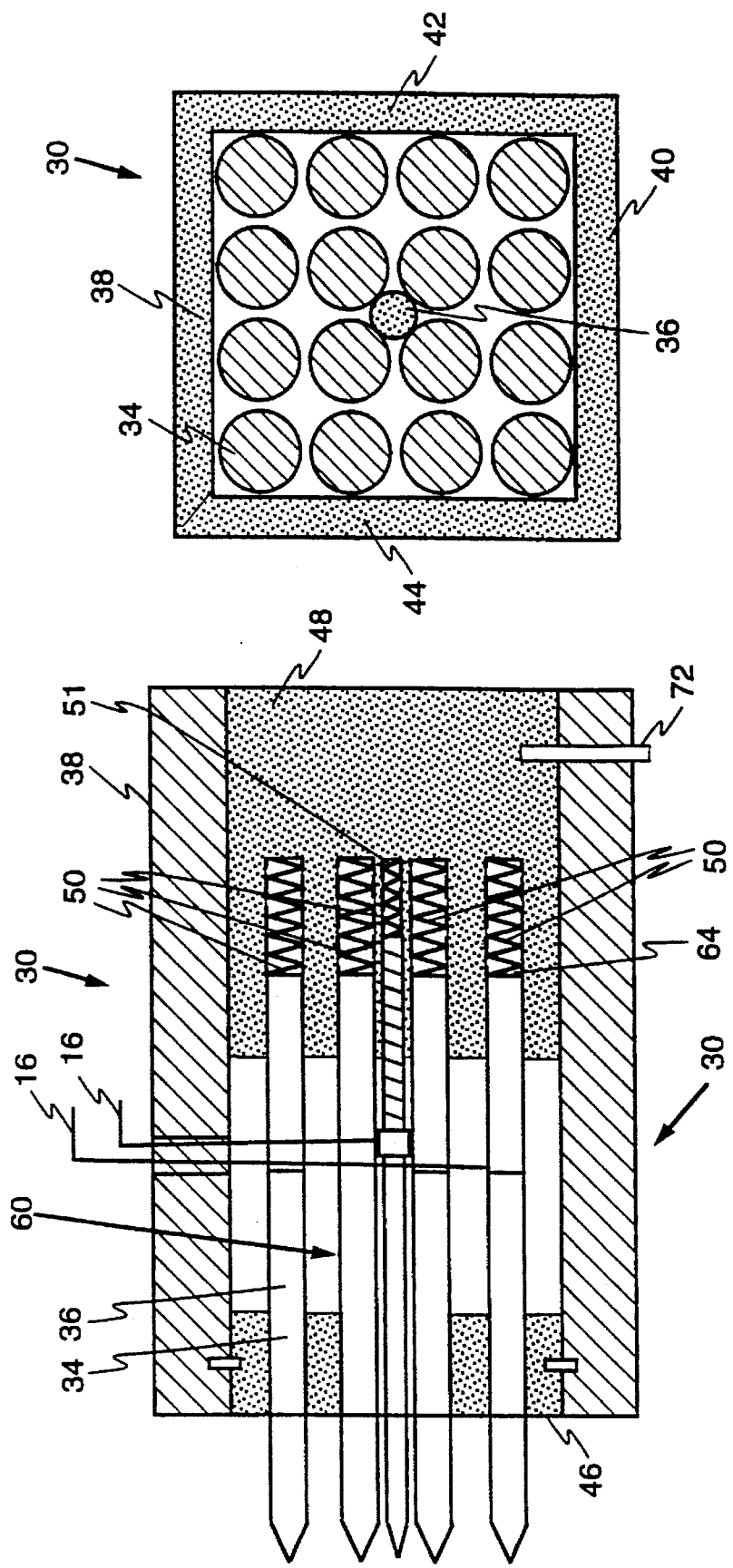

METHOD AND SYSTEM FOR DETECTING DEFECTS IN PIPES OR OTHER STRUCTURES

BACKGROUND OF THE INVENTION

The present invention relates generally to applying currents and making electrical measurements on cylindrical members such as pipes in order to detect defects therein. More particularly, it relates to facilitating the engagement or attachment of multiple electrodes or contacts to the external surface of an object, such as a pipe, and to the use of ECCT (Electric Current Computed Tomography) technology to determine defects therein.

Numerous studies have been made as part of an overall effort to improve the performance of pipes and other such structures relative to damage from flaws in the structures which can lead to defects, such as cracking, in the walls thereof. One type of degradation which has received and which deserves special attention is stress corrosion cracking. Stress corrosion cracking occurs where the pipe is utilized to contain material having high temperature, high pressure steam, water, or other fluids.

An effective way to study defects, such as cracks, which may occur within a pipe wall, is to utilize electrical measurements of the pipe and to observe and record changes in the electrical potential and flow of current in the pipe both before and after a defect, such as cracking, has been initiated and as the defect enlarges.

In order to study the cracking phenomena within pipe walls and other objects, it is frequently desirable to make numerous measurements essentially around the entire circumference of the pipe and, if believed necessary, along the entire length of the pipe from one contact point to another spaced axially along the pipe length.

When the application of a large number of current patterns and the measurement of a large numbers of voltages on a pipe can be accomplished, the data which is generated from such measurements can be analyzed by a number of techniques including Electric Current Computed Tomography or ECCT. With the aid of the numerous surface contacts attached to the pipe, ECCT provides a determination of the pipe condition as derived from such electrical measurements.

Accordingly, a problem with the use of the ECCT technology in specific, and any crack monitoring technique in general, is that a large number of electrical contacts must be precisely applied to the pipe surface in order to permit the application of current, the measurement of voltage and other critical data that is collected. Commonly owned U.S. Pat. No. 4,982,154, which is expressly incorporated herein by reference, teaches one method and application for rapidly attaching to and removing a large number of electrical contact points from a cylindrical surface, such as a pipe. Once a fixture having a plurality of electrical contact points is attached, pneumatic activation was used in the commonly owned patent, to provide the pressure to achieve and sustain contact between individual contact points and the pipe surface.

With regard to making potential measurements for ECCT technology in specific and electrical potential crack monitoring method in general of piping, a reliable electrical contact for each of the many contact points on a pipe surface is required. For contact to be effective electrically, it must be one which does not change over time (i.e., firm and difficult to move during the testing). Further, it has been found to be most effective if the contacts are essentially evenly spaced both along the pipe surface and about the pipe circumference in order to provide the proper geometry required to accumulate the data needed for an ECCT analysis and study. Once the regular geometric array of electrical probes is firmly attached to the surface of the object or pipe, different levels of current and voltage can be applied to and/or sensed therefrom.

The commonly owned patent did not specifically address variations in the surface contact resistance that would occur between different probes. If groups of probes are tied together electrically (to create a single electrode), current preferentially flow through the pin/surface interface that provides the least resistance. This condition would make mathematical modeling of the pin/structure interaction impossible because the details of the surface phenomena would be required to develop an accurate model since a predictable, repeatable distribution of current among the pins is a requirement. Thus, if there is resistance differences between the pins, problems arise making mathematical modeling of the pin/structure interaction impossible.

While the apparatus and method of the aforementioned commonly owned patent solved some problems related to pipe crack analysis, several new problems specific to the new apparatus and method surfaced which made the utilization thereof impractical. First, since gas leakage around the pins appears to be unavoidable, a constant supply of pressurized air was required for the fixture. Such a constant supply required either a local pump or a pressurized gas line. Since the apparatus and method of the commonly owned patent would most likely be used in situations where such an extended complicated gas supply system would create significant inconvenience, such as piping in a nuclear reactor which is contained within the pressure vessel, it was determined that the significant inconvenience and increased cost made the invention of the commonly owned patent impractical. Second, failure of one pin seal disabled the entire fixture, since no significant pressure would be created within the pneumatic chamber. Since the apparatus and method of utilizing the pneumatic seal would be performed in locations having at best limited access, there would be no easy, convenient way to correct the disabled seal problem. The failure of any individual seal would result in the failure of the entire device causing it to have to be removed from the pipe in order to effectuate repair.

Notwithstanding, the presentations of the art discussed above, there continues to be a need for an improved method and system for detecting defects in pipes or other structures. Such a method and system would provide for the rapid and reliable attaching of one or more fixtures having a plurality of electrical elements positioned therein for use with a mathematical model in the analyzation of a pipe or other object for defects; would have individual tension means, such as a spring, for assisting the electrical elements to make individual electric contact with the pipe or other object; and would provide for uniform current distribution over the surface of the pipe or object being maintained.

SUMMARY OF THE INVENTION

While the teachings of the commonly owned patent referred to above were somewhat effective in achieving some of the above goals, the present invention is even more effective in achieving the above and other goals particularly relating to making ECCT measurements and diagnoses relating to pipe defects.

The present system and method are distinct and different from prior practice in that the rapid and reliable attachment of a large number of pin contacts to a pipe surface and their removal therefrom is greatly facilitated over both the old welded lead method and the pneumatic pressurizing method while ensuring that each pin makes a predictable (or repeatable) point contact with the pipe surface regardless of surface roughness.

In one of its broader aspects, the objects of the present invention can be achieved by providing a system and method for rapidly and reliably attaching a fixture having a plurality of electrical elements, such as an electrode having current pins, positioned therein for use with a mathematical model in the analyzation of an object for defects. A tension means, such as a coil spring, Belleville washer or equivalent is operatively connected to each individual pin which make up each electrical element. Each of the current pins is capable of conducting electricity and each has a separate electrical connection to a data collecting means.

In another aspect of the present invention, the plurality of current pins are equally spaced from one another and are operatively connected to a current source with at least one voltage pin, operatively connected to a voltage measurement means, being relatively centered to the plurality of current pins.

In one preferred and operable form of the present invention, at least sixteen (16) current pins are arranged in a 4×4 configuration with one voltage pin centered in between the innermost four current pins to constitute one electrode.

In another more specific aspect of the present invention, the voltage pin allows voltage measurements without disrupting the uniformity of the current application to the current pins.

In an even more specific aspect of the present invention, springs are used to provide a high loading force for each pin and for allowing the electrode, having sixteen current pins (16), to effectively engage uneven surfaces.

In another aspect of the present invention, a rear block, secured by any connection means, such as screws or the like, engages the electrodes and is adjustable relative to the fixture to establish sufficient loading of the individual pins in each electrode and for holding the rear block in position once the sufficient pressure has been applied to the pins contacting the surface of the object.

In still another aspect of the present invention, the rapid removal of the fixture from the object is provided for such that the spring force will return the block and pins to their original unloaded position, i.e., not under spring pressure.

Accordingly an object of the present invention is to provide a system and method for rapidly and reliably attaching and detaching electrical contacts in a pattern on a cylindrical surface, for applying current and voltage thereto and for taking electrical measurements thereof.

Another object is to provide a system and method for making a large number of contacts in an accurate geometric pattern which allows the accumulation of data for analysis by Electric Current Computed Tomography or other crack monitoring techniques.

A further object is to provide a system and method for the rapid and reliable positioning of a large number of contacts to a pipe surface and for the quick disengagement of the contacts from the pipe surface and the rapid and reliable reattachment at another selected location on the pipe surface.

Yet another object of the present invention is to provide a system and method for evaluating pipes having rough surface for defects.

Still another object of the present invention is to provide a system and method which results in uniformity of current flow through each of the individual pins that constitute an electrically connected group or electrode.

Still yet another object of the present invention is to provide a system and method that results in the quick, accurate adjustment of pressure for each individual electrical on the pipe surface.

Other objects and advantages of the invention will be apparent from the following description, the accompanying drawings and the appended claims.

BRIEF DESCRIPTION OF THE DRAWINGS

FIG. 5 is a section view taken along line A—A of FIG. 4;

FIG. 6 is a section view taken along line B—B of FIG. 4;

DETAILED DESCRIPTION OF THE INVENTION

Figure 1:
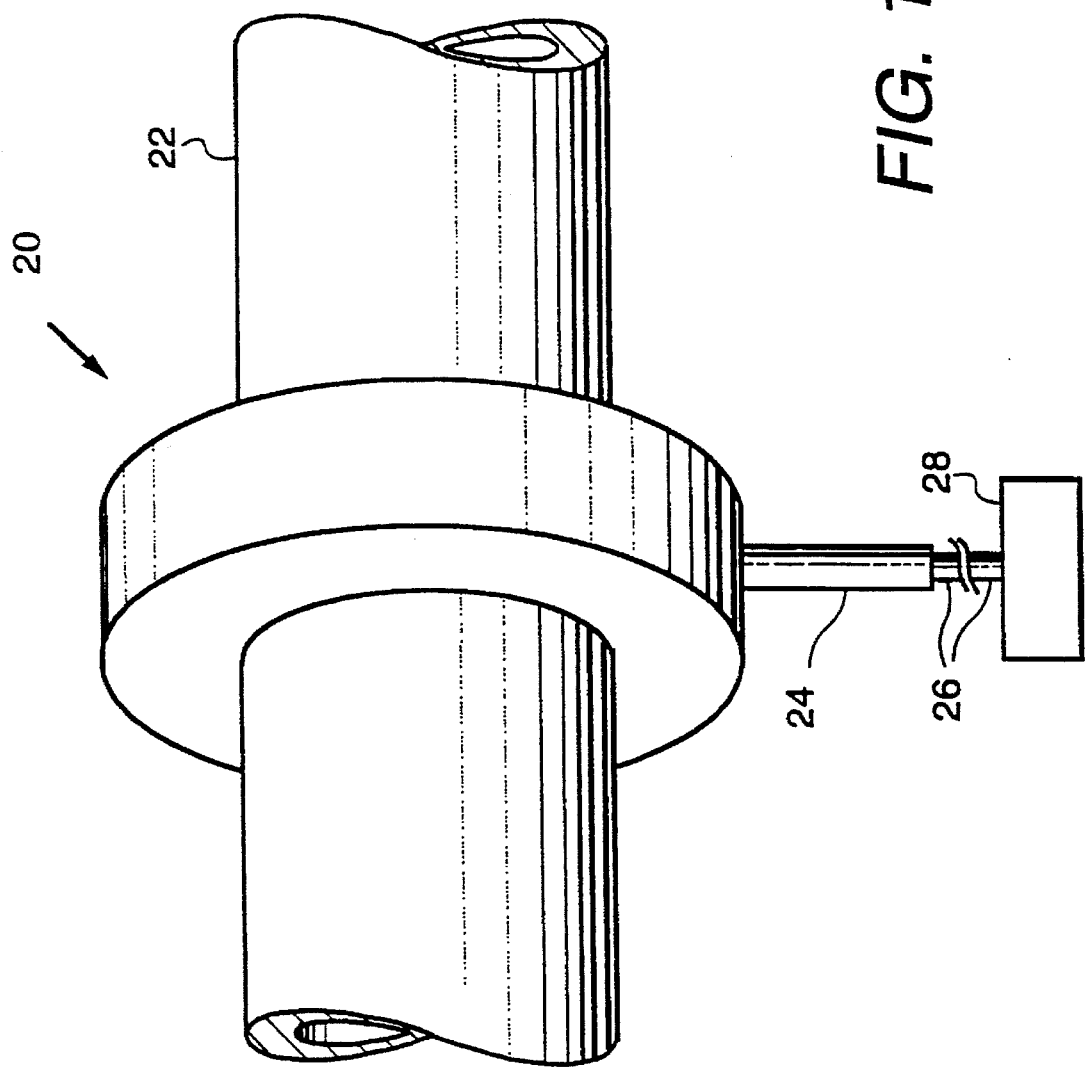
FIG. 1 is a perspective side elevation of an electrode fixture as provided pursuant to the present invention with a pipe extended through the opening thereof.

As discussed in the above-mentioned commonly owned patent, Electric Current Computed Tomography (ECCT) is a somewhat new technology directed toward examining the internal structure of pipe walls and other metal objects. By applying a set of electric contacts to a structure, by applying electric current flow through the structure and by measuring voltages from one contact point to another, ECCT provides graphic electronic representation of the structure. Greater resolution of the pipe structure is achieved by the greater the number of contact points provided.

Additionally, the precise location for the contact points has been found to be important in order to accurately locate any defects. For example, if current is supplied to a single contact over an area of one square centimeter, it is difficult to tell precisely where within the square centimeter the electrical contact occurs. If, however, there are separate electrical contacts for every square millimeter of the square centimeter, the current can be more uniformly distributed over the surface at precise locations. The voltage, in turn, can be measured at a single non-current carrying point achieving relatively greater precision in determining the structure of the object being analyzed.

It is known that the ECCT technique requires electrodes with a uniform current flow over a large area. Individual point contacts within an electrode as opposed to a single large electrical contact provide a plurality of uniform contact points between each electrode and the pipe surface. Therefore, the electrode concept having a plurality of pin point contacts is preferred in that each contact makes firm, uniform electrical contact with the surface.

Pursuant to the present invention, as was the case in the commonly owned patent, a multiplicity of electrode contacts are made with the external surface of an object. Each of these point contacts is made by individually urging a pin point to engage the surface of the object at a precise contact location. By having a relatively small contact area for each pin in each electrode, precise location can be achieved quickly and reliably. Precise location at acceptable pressure is also achieved by having the pin points of each electrode accurately guided and held in position as they are urged against the object surface, such as a pipe.

Basically, the system and method involves using a large number of hardened and sharply pointed metallic pins held in an electrically-isolated ring housing somewhat larger in diameter than the object, such as a pipe, being monitored. The pins are allowed to slide snugly in the electrodes in a radial direction so that the pins can engage the pipe. The outer end of each pin extends from the front block to the rear block and has a spring operatively positioned thereon. Current or electrical potential leads attached to each pin are directed through the walls of the fixture in an insulating member and routed to a current generation and data collection box 28.

With the application of sufficient spring pressure to each pin, each pin is driven radially inward to engage the surface of the pipe and to establish electrical contact therewith. Removal of the pressure by means of the adjustment device releases the pins and allows for removal from or repositioning of the fixture on the pipe.

In various applications of electrical potential methods for measuring crack growth or ECCT measurements, it is important to accurately know the position of each current and potential electrode relative to some reference position on the pipe. Accurate location of each lead by the earlier procedure of spot welding is difficult due to the numerous number of contacts that must be made. Positioning of the electrodes can be performed reasonably accurately by the prior art spot welding methods only when the pipe is cylindrical and the surface is smooth as by means of a scribed grid and could only be accomplished in the laboratory. However, when the pipe surface is rough, and in particular, if a prior art welding technique is employed, positioning of the probes is difficult. However, by using the method described herein and in the commonly owned patent, each pin electrode makes a point contact with the pipe surface regardless of surface roughness. Further the circumferential and axially position of each electrode depends only on the pipe diameter and on the dimensions of the non-conducting ring and can be determined to at least 0.002 inches.

The main reasons that the prior spot welding is not appropriate for the technique or for field locations described herein are:

(1) too many leads to be practically attached to the pipe due to the physical and processing constraints, and (2) the accuracy of spot welding at specific locations on pipe is insufficient when welding is performed at the site (in the field).

With the system and method of the present invention it is extremely easy using remote means for shifting the fixture to another position on the pipe and to reestablish the contacts even during on-going operations.

As is indicated above and referring to the commonly owned U.S. Pat. No. 4,982,154, what is sought was and is a system and a method for quickly and reliably attaching and removing a large number of current and electrical potential probes to and from a pipe or other cylindrical solid. Such attachment should provide for the introduction of current paths and for the measurement of electrical potential compatible with ECCT (electric current computed tomography) technology and techniques.

In particular, the system and methods described herein provide simpler and less time consuming, as well as reducing the tedium and risk associated with spot welding electrical leads pipe structures as had been used in the art. Further, it is believed that the present system and method is even more reliable and accurate than the previous gas inflated sealed system of the commonly owned patent. The gas pneumatic system may be subject to failure due to gas leaks at defective seals or from accidental tube punctures. It is believed that the present invention, with its individually adjustable pressure springs, is much less likely to fail. If it does fail, it is most likely that continued operation of the remainder of the fixture could occur and that repairs to the fixture should require only the replacement of the individual failed electrode, as opposed to the entire tube as well as having to reinsert all the individual pins into the new tube of the system of the commonly owned patent.

Moreover, the accomplishments of the present invention have been verified by an experimental demonstration on a stainless steel pipe using the system and method herein disclosed to produce a usable diagnosis of a machined defect in a pipe.

As is evident from the above commonly owned patent, the underlying system and methods involve using a large number of hardened and sharply pointed metallic pins which are held in a ring fixture somewhat larger in diameter than the pipe. The pins are engaged to the outer surface of the pipe by application of force thereto. Also, pursuant to the present invention, current and electrical potential leads are attached to each pin and these leads extend out of the pin holding fixture and are electrically connected to a central interface region.

Due to the presence of uneven surface in pipes and other objects, it is important that the pins be urged against the pipe surface with sufficient loading force to provide adequate contact between the pins and the pipe surface regardless of the relative roughness of the surface. By sufficient contact, we mean that current is flowing between the pin and the pipe being monitored. If the pin does not touch the pipe surface, there is no current flow. If the pipe has a film or grease from an oxide, or the like, on its surface, with insufficient load force, the current might arc.

Due to the variation and the contraction of the spring or spring means and the resulting pin force, which occur due to the roughness of the structure surface and the curvature of the structure surface, spring means, such as coil springs, should be selected so that a sufficient force of approximately 2 to about 3 pounds would be applied to each pin at the contact point with the pipe. The pin can preferably be made of a steel which will not yield under the applied pressure. The points of each pin should be hardened to minimize the deformation of the pin tip during the application of the contacting force. The pins and pin tips should be small enough so that contact occurs within a region that is significantly smaller in size than the spacing between individual pins. The pin material should also be selected such that the electrical resistance of the pin material is not significantly greater than the electrical resistance of the material which composes the structure being analyzed.

As shown in FIG. 1, a generally circular electrode attachment fixture 20 operatively connected a pipe 22 is illustrated. The fixture 20 is positioned at a location along pipe 22 for taking measurements in an effort to learn of the serviceability of the pipe at that point. It should be understood that only one electrode attachment fixture is shown for the purposes of clarity, but that any number of such fixtures could be positioned on a pipe simultaneously.

The electrode attachment fixture 20 includes a conduit 24 extending therefrom. Electrical conductors 26 extending from the interior of the fixture to an external circuit generation and data collection unit 28 are housed therein. At this point, it should be noted that one of the principal differences between the present invention and that contained in the earlier commonly owned '154 patent is the absence of any pneumatic tube contained in the fixture or gas supply and delivering means which had been used to pressurize the interior of the fixture and move and hold the electrode in contact with the pipe surface.

Figure 2:
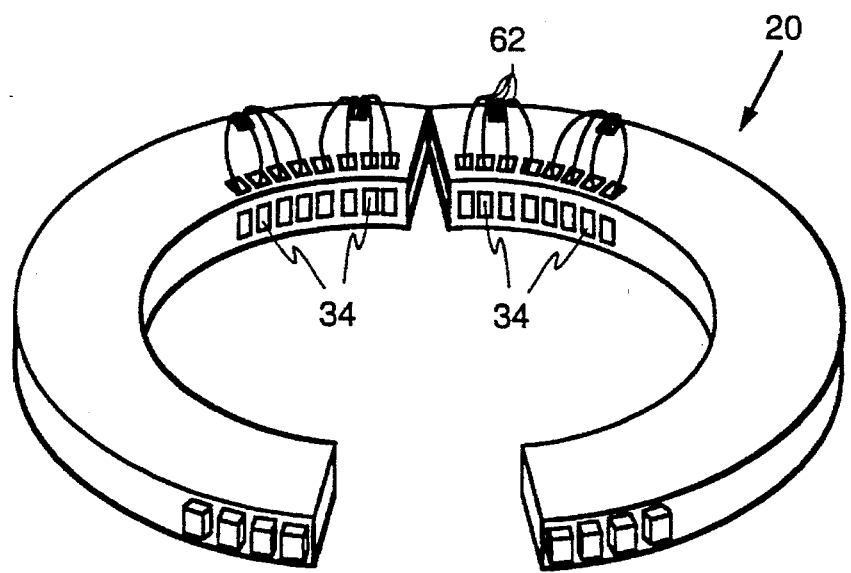
FIG. 2 is a partial perspective side elevation with portions removed of the electrical attachment fixture partially opened.

As shown in FIG. 2, the electrode attachment fixture 20 opens up like a clam shell to provide for positioning of the fixture on a pipe or other object. This particular attachment fixture 20 contains sixty-four (64) electrodes 30. Each electrode 30 contains sixteen (16) current carrying pins 34 and one voltage measurement pin 36 (see FIGS. 3 and 4). The inner diameter of the fixture corresponds approximately to the outer diameter of the pipe 22 or object being evaluated.

Figure 3:
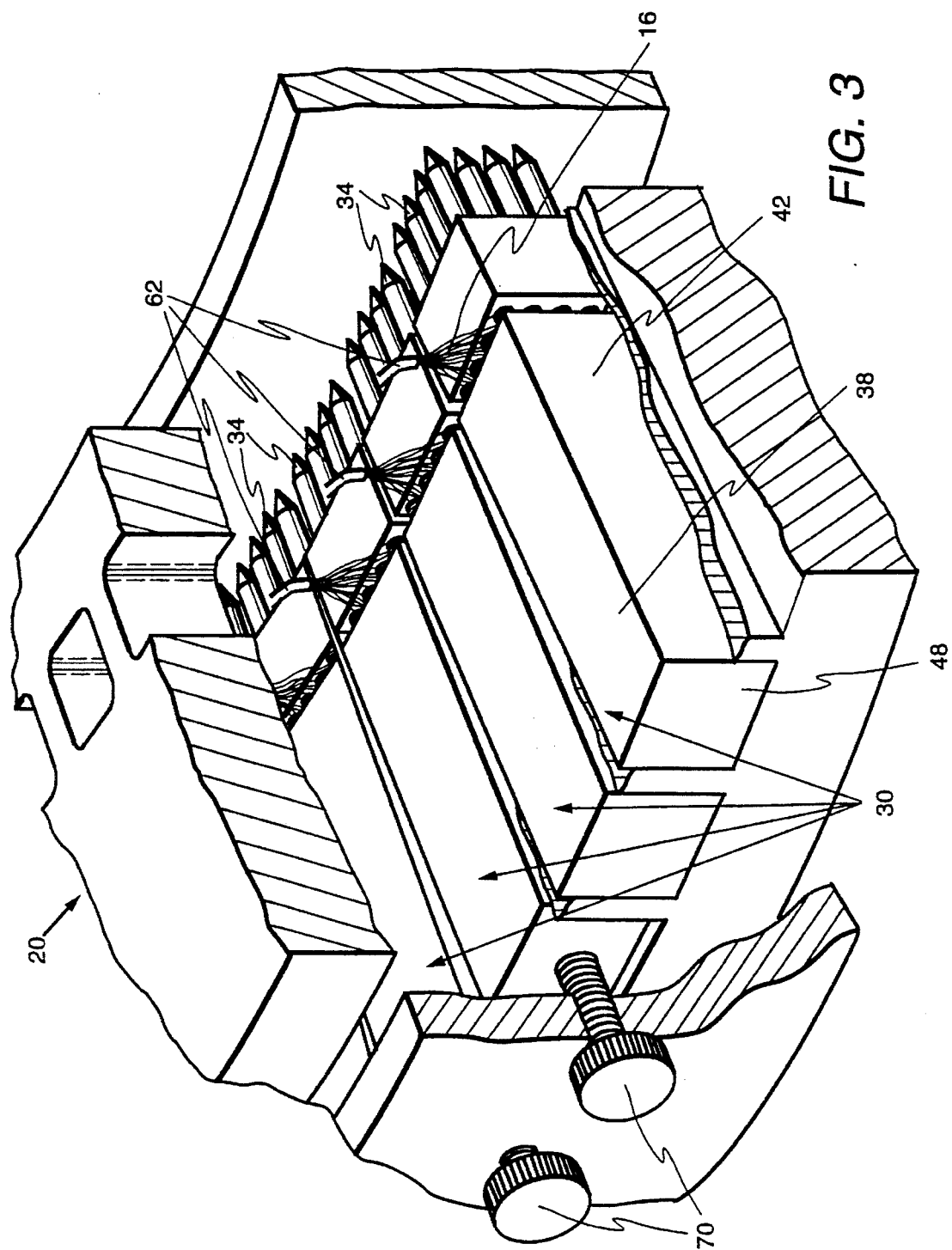
FIG. 3 is a partial perspective cut away detailed view of electrodes positioned in the fixture of FIGS. 1 and 2, contacting a pipe.

As clearly shown in FIGS. 2 and 3, the interior of the fixture 20 houses a plurality of current carrying pins 34 in each electrode 30. As more clearly shown in FIGS. 3, 4, and 5 the pins 34, 36 are housed in the electrode 30 composed of a top 38, a bottom 40 and two side walls 42, 44. The sixteen (16) current pins 34 are equally spaced about a center voltage pin 36. A front guide block 46 is positioned at one end of the electrode 30 and has provisions for the sixteen (16) current 34 and one voltage pin 36 to extend therethrough. The electrode rear block 48 provides the surface against which the springs 50, attached to each of the current pins 34 and the one voltage pin 36, used to urge the pins 34, 36 forward out of the front guide block 46.

As seen more clearly in FIG. 5, a cavity 60 between the front guide block 46 and the rear block 48 is provided to accommodate the attachment of current and voltage lead wires 16 to the pins 34, 36 and to outside terminals (not shown).

As shown in FIGS. 2 and 3, insulation means 62 contain the wires connected to the current carrying pins 34 and to the current generators (not shown) within the insulation means is a wire 16 to each current pin that is, for illustrative purposes only, about 6.00 inches long, about 10 mil diameter and is composed of about 80 percent nickel and about 20 percent chromium wire. This particular length and composition of wire provides a resistance of approximately 3 ohms. It is this fixed resistance in series with the central current connection and the individual current pin 34 that provides a uniform current distribution through the electrode 30. The magnitude of this resistance is much larger than the resistance of the pins, the pipe, and the surface contact. This particular dimensioned wire and the resistance current assures that variations in surface contact do not significantly affect the uniformity of the applied current between the individual pins 34 that are electrically connected to one another (see FIG. 8).

As stated above, the specific dimension given above have been used, but are for illustrative purposes only. The above specifics were designed to provide a large electrical resistance between the point of current joining and the individual pins. Clearly, there are an infinite number of equally acceptable designs which would result in acceptable results. The resistance of the wire is designed to be at least an order of magnitude greater than the resistance from the point of contact between the wire and pin to the structure being tested. This resistance includes a resistance drop along the pin and the contact resistance between the pin and the structure.

Figure 7:
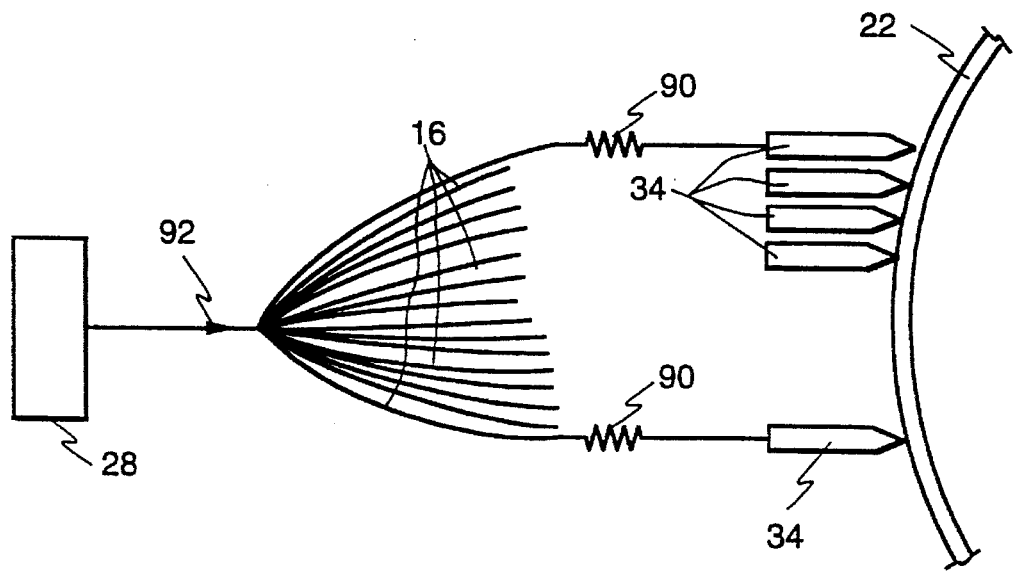
FIG. 7 is a graphic representation of the current flowing through the respective wires to each individual pin of the present invention.

In the specific illustration of FIG. 7, it was important that the resistance 90 placed between the current source and each individual pin 34 be of an order of magnitude sufficiently larger that at least the resistance of the rest of the system between the electrode tie-in 92 and the structure 22 being monitored. In the particular test, the order of magnitude of resistance 90 added was approximately about 20 to about 25. It is believed that an order of magnitude of 10 would be sufficient and that any order of magnitude above 25, limited only by the upper limit of the current, would also work.

Each of the current pins 34 has a spring means, illustrated as a coil spring 50 (FIGS. 4 and 5) positioned between its internal end 64 (FIG. 5) and the rear block 48. As shown in FIG. 6, preferably the sixteen (16) current pins 34 are arranged in a square 4×4 configuration with a voltage pin 36 in the very center of the configuration. The center voltage pin 36 has the advantage of providing a voltage measurement without disrupting the uniformity of the current application.

The basic concept is that the current pins 34 create a complete uniform array of contacts with the pipe or structure surface 22. The voltage pin 36 is positioned in between a set of current pins 34. For example, an alternate approach might be to use a 5×5 array of pins, where the center pin measured the voltage and the remaining 24 pins supplied current. This approach would not provide a uniform current application. The current applied would be zero at the middle of the array. The key is to have the voltage lead assume an interstitial location in a uniform array of current pins. It is believed that even numbered arrays provide the uniformity of current application necessary to make the technique operate effectively, because with odd number arrays, it would be necessary to remove a current pin in order to insert a voltage pin in the middle of the array.

As shown in FIG. 3, four of the individual electrodes 30 are mounted in the electrode attachment fixture 20. The top and rear walls of the fixture are shown as well as the adjustment devices 70 for positioning each electrode 30 within the fixture 20. FIG. 3 illustrates one potential specific arrangement of the electrode attachment fixture 20, but recognizes that other configurations and arrangements are possible.

With regard to the pin diameter, it is believed optimum to have the smallest pin diameter possible, independent of the actual pipe diameter. The pin diameter is limited by both the strength that support a sufficient contacting force and the size required to practically assemble the fixture.

The contact pressure must be large enough to provide sufficient contact between the pin and the structure or pipe. This pressure depends on the roughness and cleanness of the pipe surface. The only limits to the amount of the contact pressure is the strength of the pins and the deformation of the pin tip.

While the fixture was constructed and the tests were conducted utilizing coil springs 50, it is believed that Belleville washers or other appropriate spring means which apply sufficient force over a range of displacements could be utilized.

As the diameter of the pipe is increased, the size of the fixture 20 must increase. Since clearance must exist between the pipe 22 and the fixture 20, small pins 34 are preferred for any pipe diameter. As the pipe diameter increases, it should be possible to have more pins 34 and more electrodes 30 for fixed pin/electrode dimensions. Extra pins/electrodes would improve the resolution and detection capability of the monitoring technique.

The electrode attachment fixture 20 has a conduit 62 extended therefrom for connecting the electrical conductors 26 from the interior of the fixture 20 to the external current generation and data collection unit 28 (See FIG. 1).

Figure 4:
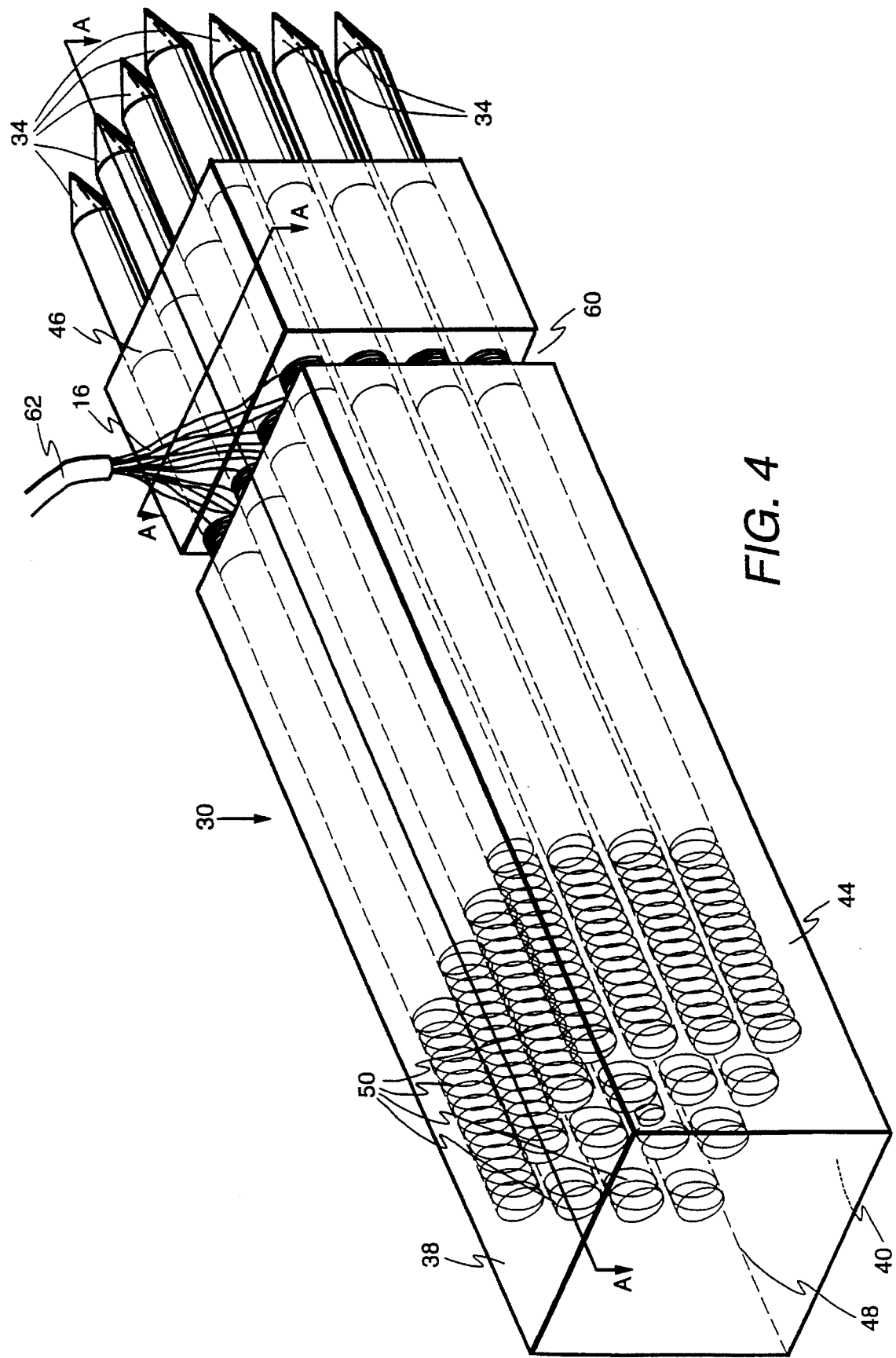
FIG. 4 is a perspective view of a single electrode as used in the fixture of FIGS. 1 and 2.

A single electrode is illustrated in FIGS. 4, 5, and 6. The single electrode 30 has sixteen (16) individual current pins 34, and one centrally located voltage pin, 36. A single coil spring 50 is positioned relative to the blunt end 64 of each pin 34, 36 and the rear block 48 of the electrode for urging the pins forward through the front block 46 and subsequently into contact with a surface.

As clearly shown in FIG. 5, electronic connections 16 for current distribution and voltage measurement are made to the appropriate pin. The rear block of the electrode is preferably held in position by a holding pin 72. The voltage pin 36 of each electrode is positioned in the exact center of the 4×4 array of current pins 34.

Since each pin 34, 36 is individually urged forward toward the center of the fixture 20, the current pins most proximate the voltage pin and the voltage will probably receive more compressive forces than the most remote current pins due to the curvature of the object or pipe 22 being monitored.

The system and method of the present apparatus was tested by building the fixture 20. The fixture frame, as built, was made of aluminum and the back and front blocks are made of Plexiglass. The current and voltage lead wires were 0.010 inch 80-20 Nichrome wire and the pins were tempered carbon steel. The voltage pins 36 have an outer diameter of 0.055 inches with an approximately 0.125 inch taper at the leading end. The current pins 34 had an approximate outer diameter of about 0.079 inches with about a 0.0625 taper at the loading end. The loading end of the current pins 34 also has about a 0.0015 inch radius to prevent the bending of the pin tip. The springs 51 used to urge the voltage pins have a spring constant of about two pounds per inch so that about 0.5 pounds are applied to each pin during electrode attachment. The springs 50 used for the current pins 34 had a spring constant of about twelve pounds per inch so that about two to about three pounds per inch pressure was applied to each pin in contact with a surface.

Two studies were conducted analyzing the performance of the disclosed system and method. In the first study, a separate fixture was built to provide contact between a single electrode and a flat plate. Current leads were attached to each pin and a grounding lead was attached to the flat plate. Force was applied to a loading block by turning a screw. The individual pin leads were wired together using different resistive circuits. Current was directed into the main lead through the pins to the flat plate and out to the ground. While current was flowing through the pins, the voltage drop across each pin was measured. This voltage drop had been previously calibrated so that this voltage difference could be converted into a measure of the portion of current flowing through each pin.

Figure 8:
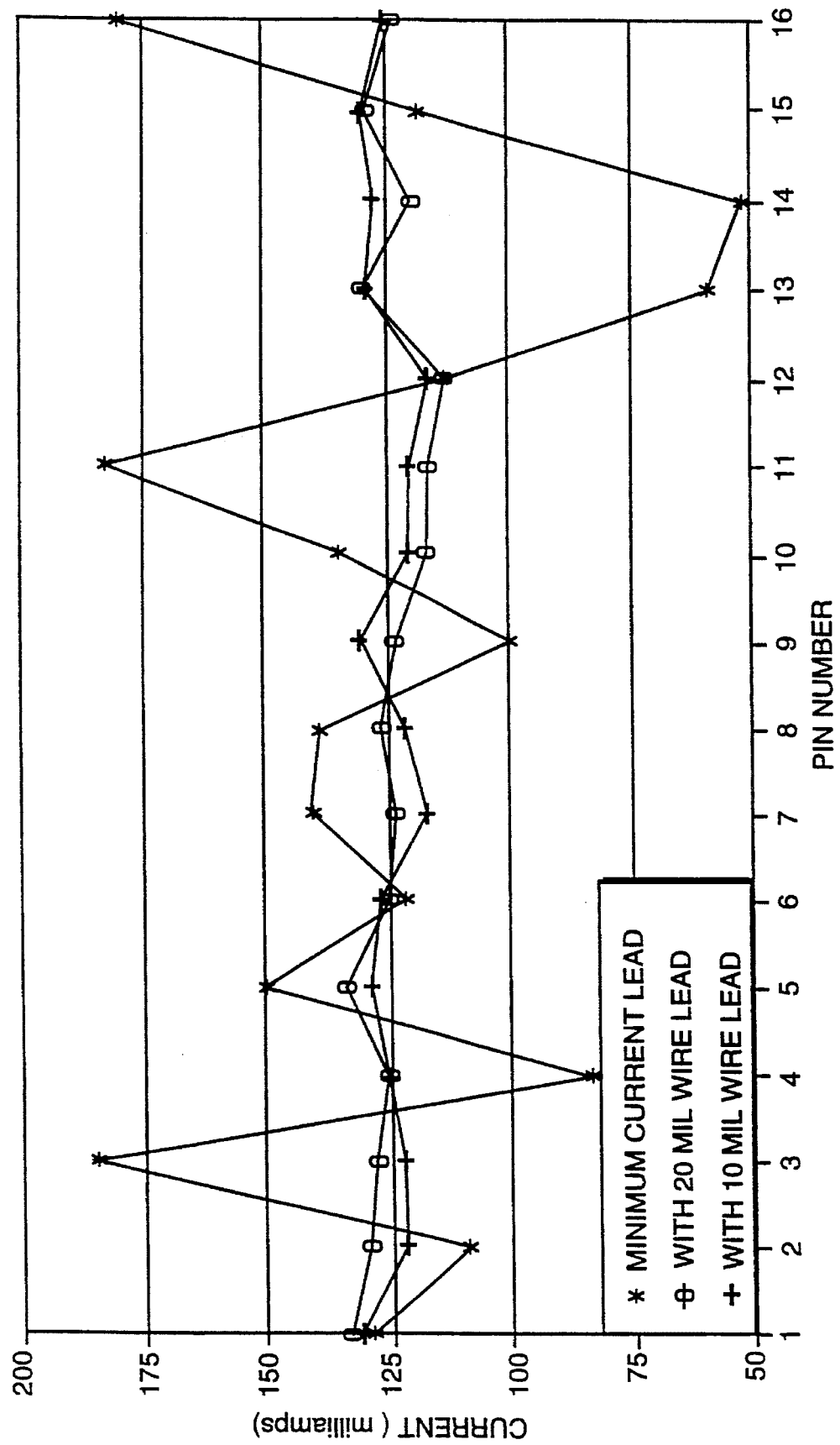
FIG. 8 is a graphic representation of the current passing through individual pins that are electrically connected.

As shown in FIG. 8, a plot of the pin currents is illustrated. One set of data depicted was measured using no additional resistance in the circuit. A six-inch piece of 10 mil diameter 80-20 Nichrome wire was then placed in series with each of the pins. This wire provided approximately three ohms of resistance to each pin. This resistance was large enough to offset variations in the resistance among each pin and at the pin-plate contact plate. The uniformity of this path resistance resulted in an increased uniformity of current flowing through each pin. Also included in FIG. 7 is the current distribution with twenty mil diameter wire. The uniformity in the electrode currents will allow the interaction between the electrode and the contacting solids to be more uniform between applications of the electrode to different solids and more easily modeled in ECCT imaging algorithms.

Without the added resistance 90, the amount of current that would flow through each individual pin 34 would depend on the contact resistance between the pin and the structure. This resistance would be affected by the applied force, surface contamination, surface oxide and surface roughness. The addition of a carefully calibrated series resistance 90 assures that the current will be distributed among the pins in a predicable, repeatable fashion. Since mathematical modeling of the electrode-structure interaction is used for the ECCT technique, this predictable and repeatable behavior is important.

Another series of tests was conducted using the complete 64 electrode attachment ring 20. The test was conducted in an effort to detect and image defects in a sample boiling reactor pipe. The fixture was attached to a section of a 304 stainless steel schedule-eighty pipe (10.7"OD and 9.7"ID). Defects were machined into the surface of the pipe's inner wall. Detection studies were performed for different size machine defects and the ECCT technique was used to make images of the defects. The detection studies were performed by applying current patterns to the pipe through the multipin electrodes and measuring the resulting voltage distribution.

Figure 9:
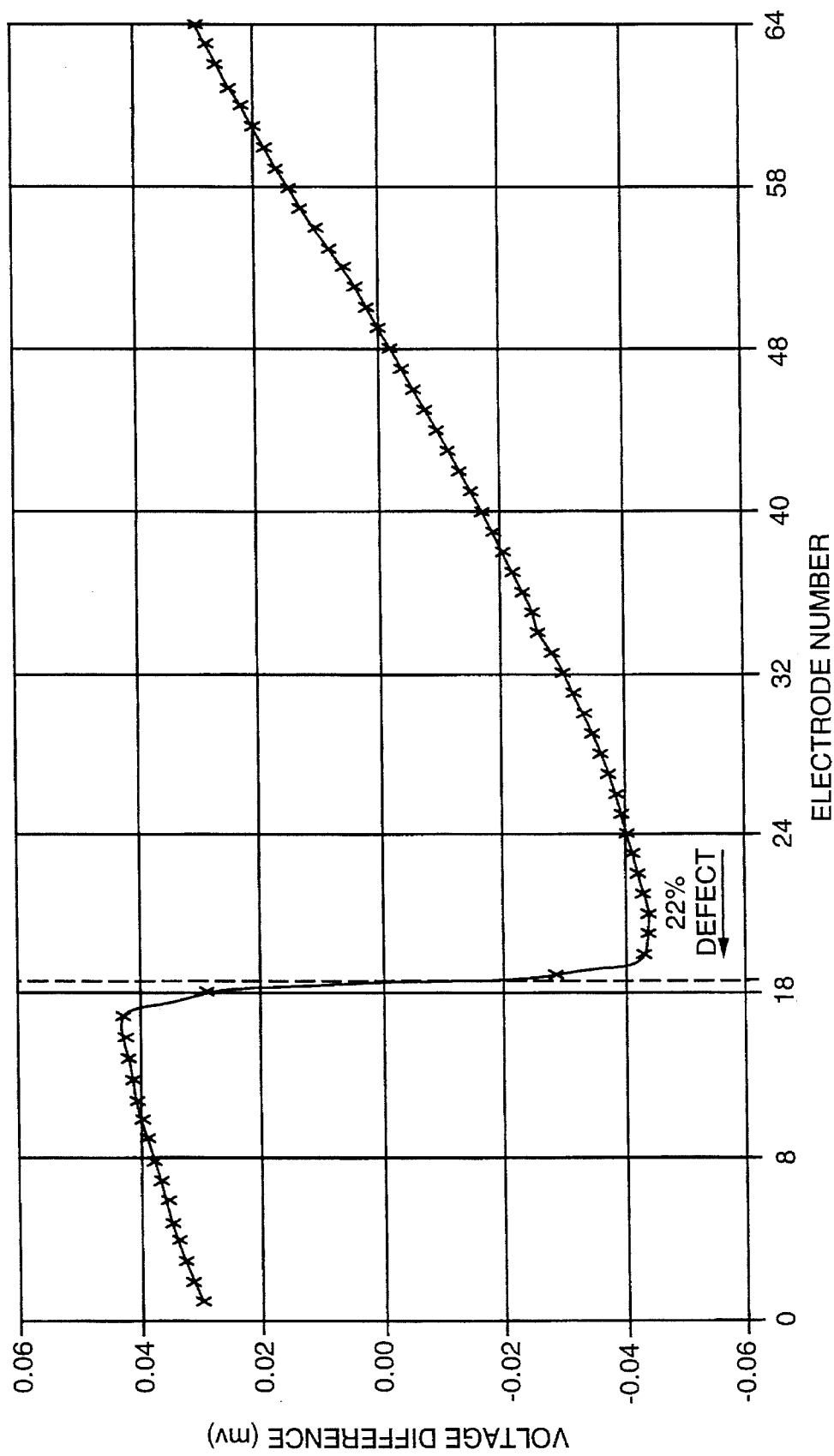
FIGS. 9–11 are graphic representations of pipe defects detected by the system and method of the present invention.
Figure 10:
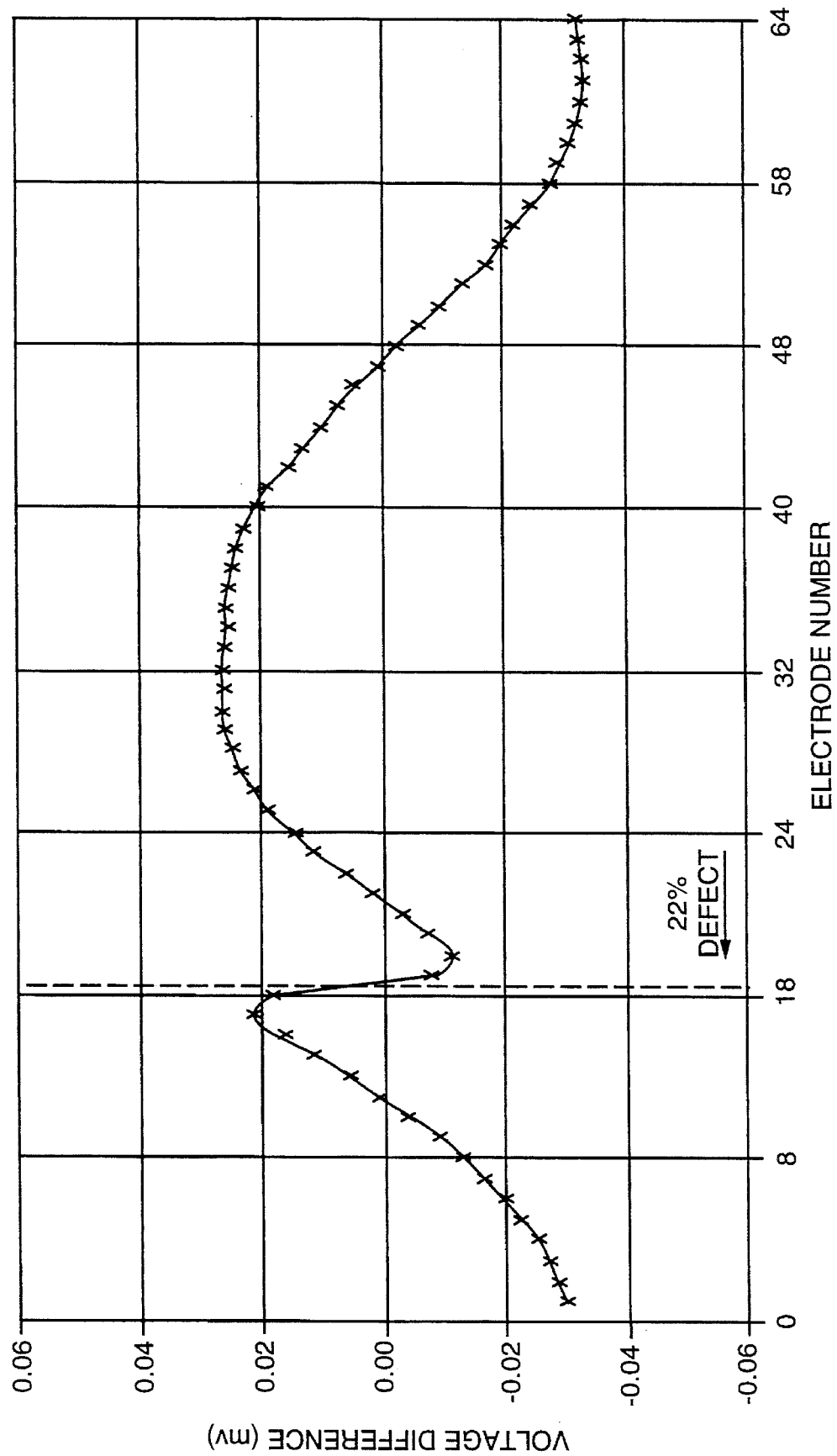
Figure 11:
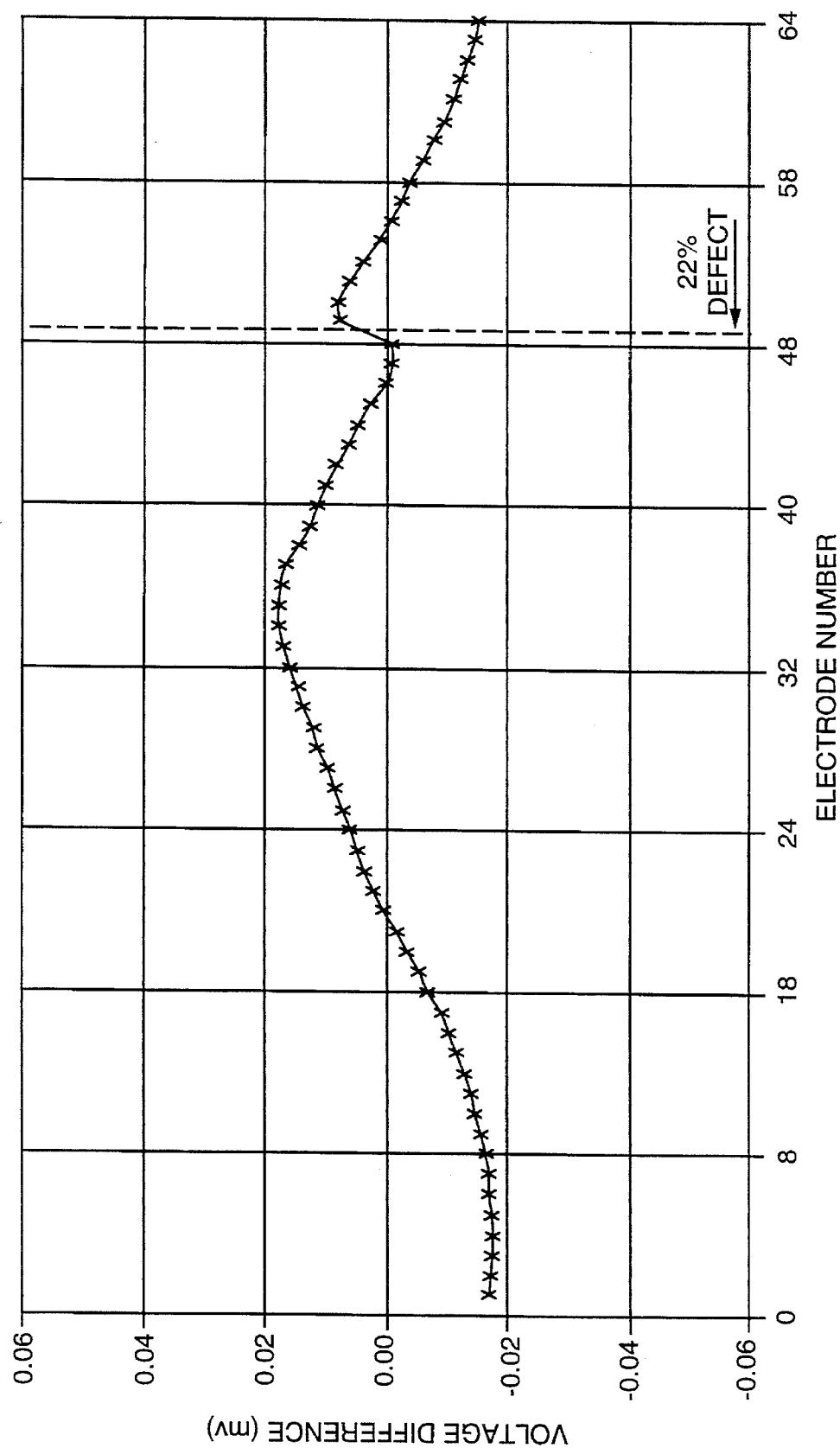

A defect was machined into the pipe and the measurement procedure was repeated. A comparison of these two voltage distribution can be use to provide indications of defects size and locations. FIGS. 9–11 are graphic illustrations of plots of these voltage differences of defects of 5, 12 and 22 percent wall thicknesses. These plots appear to provide clear indications of the defects existence, location and size.

Figure 12:
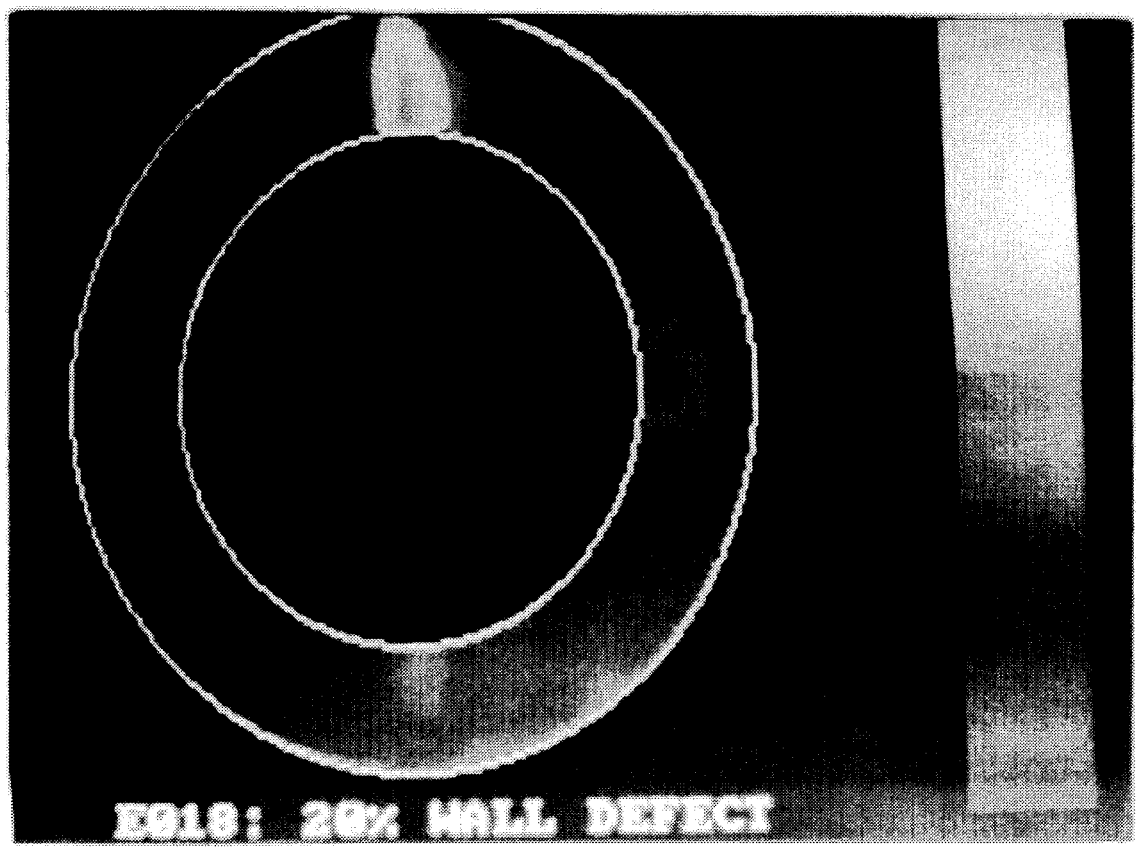
FIG. 12 is a representation of a defect image utilizing the electrode attachment fixture and ECCT technology of the present invention.

An imaging study was performed using a technique similar to those above. The only difference was that a set of current patterns (63 patterns for a 64 electrode system) were sequentially applied to the pipe. During each of these current patterns, the voltage distribution on the pipe outer surface was measured by the voltage pins. Using applied current and major voltage data, the ECCT technique was used to make an image of the resistivity distribution in the pipe interior. This image is illustrated in FIG. 12, which shows a clear indication of the 22 percent pipe wall defect.

Finally, the quality of defect imaging with ECCT is directly related to the amount of exterior surface on which the currents are applied. Therefore, it is important that each electrode be space-filling, with little empty space between adjacent electrodes. This particular type of electrode design requires uniform electrical contact at the solid surface over a large area.

The present system and method solves the problem of defect imaging with ECCT by utilizing sixteen (16) individual pins current pins each pressing with sufficient pressure into the solid surface to make effective contact to give a discrete uniformity, achieved by a nearly uniform distribution of current by applying currents at discrete points, that is possible to mathematically model. Additionally, the additional series resistance 90 attached to each current carrying pin 34 resistance circuit (shown in FIG. 7) helps assure the uniformity of the current flowing through each current pin within an electrode 30 has made ECCT analyzation more practical.

As stated earlier, the principal difference between the commonly owned '154 patent and the present system and method revolve around the replacement of the '154 pneumatic device tension method by individual pin springs for providing the contact force between the pins and the object surface and the significant series resistance used between the current leads and the pins to help assure uniformity of current within each electrode. This particular construction and method has been successfully used and applied to defect imaging with ECCT techniques, as shown in FIG. 11.

Therefore, it appears from the above description that all objects of the present invention have been met.

While the method or the system and method herein described constitute preferred embodiments of the invention, it is to be that the invention is not limited to this precise system and method, and that changes can be made therein without departing from the scope of the invention which is defined in the appended.

What is claimed is:

1. A system for detecting defects in an object having a cylindrical surface, the system comprising:

a plurality of multiple pin electrodes sufficient to cover the circumference of the cylindrical surface, each multiple pin electrode having a single voltage pin and at least three (3) current pins contained therein;

structure for operatively positioning the electrodes relative to the object and in contact with the cylindrical surface; and tension means, operatively connected to each pin, for urging the pins such that contact with the cylindrical surface is sufficiently equal between pins wherein a mathematical model can be utilized to analyze the object for defects.

2. The system of claim 1, wherein the structure for operatively positioning the electrodes in contact with the cylindrical surface is a spring means.

3. The system of claim 2, wherein the spring means is a coil spring.

4. The system of claim 2, wherein the spring means is a Belleville washer.

5. The system of claim 1, wherein one of the plurality of multi-pin electrodes comprises:

a plurality of current pins equally spaced from one another and being operatively connected to a current source; and at least one voltage pin, operatively connected to a voltage measurement means, and being centered relative to the plurality of current pins.

6. The system of claim 1, wherein one of the plurality of multi-pin electrodes comprises:

a first block for controlling individual pin positions;

a second block;

a cavity, operatively positioned between a first and second block, wherein current and voltage leads are attached to the pins and to outside terminals; and wherein the tension means further comprises:

a plurality of springs, at least one spring for each pin, for transferring the load from the second block to the pins.

7. The system of claim 6, wherein one of the of multi-pin electrodes further comprises:

more than 3 current pins.

8. The system of claim 7, wherein the voltage pin is positioned in the relative center of the current pins.

9. The system of claim 7, wherein the voltage pin provides for voltage measurements without disrupting the uniformity of the current application to the current pins.

10. The system of claim 7, wherein as many as 64 multi-pin electrodes are utilized in the system to conduct detection studies.

11. The system of claim 5, wherein a resistance is positioned in series between each current pin and the current source.

12. The system of claim 11, wherein the resistance is at least 10 times greater than the contact resistance between the current pin and the structure being monitored.

13. The system of claim 11, wherein the resistance is about 10 to about 25 times greater than the contact resistance between the current pin and the structure being monitored.

14. Apparatus for making a multiplicity of electrical contacts about the surface of a cylindrical object comprising:

a plurality of multi-pin electrodes sufficient to cover the circumference of the cylindrical object, each multiple-pin electrode having a single voltage pin and at least three (3) current pins contained therein;

structure for operatively positioning the electrodes relative to the object and in contact with the cylindrical surface thereof;

a multiplicity of pointed metal conducting contact pin elements each having an electronic lead connected thereto operatively positioned in each electrode;

structure, operatively connected to each individual pin, for maintaining each pin in contact with the surface of the cylindrical object at a pressure and location sufficient to allow useful data collection by Electric Current Computed Tomography.

15. The apparatus of claim 14, wherein the maintaining structure comprises a spring means.

16. The apparatus of claim 14, wherein the pins are formed from steel drillrod.

17. The apparatus of claim 14, wherein each pin has a diameter of about ⅛ inch.

18. The apparatus of claim 14, wherein the pressure of the maintaining structure is sufficient to apply a contact force of at least about 300 grams to each pin.

19. The apparatus of claim 14, wherein each electrode has, within an area of about ½ inch by at least ½ inch, at least 16 pins, each pressing about equally on the surface of the cylindrical object.

20. The apparatus of claim 14, wherein the maintaining structure is a Belleville washer.

21. The apparatus of claim 14, wherein the data collection pressure structure is a coil spring.

22. The apparatus of claim 14, wherein the pressure each pin exerts on the object surface is about 300 grams per square inch.

23. The system of claim 7, wherein a resistance is positioned in series between each current pin and the current source.

24. The system of claim 23, wherein the resistance is at least about 10 times greater than the contact resistance of between the current pin and the structure being monitored.

25. The system of claim 23, wherein the resistance is about 10 to about 25 times greater than the contact resistance between the current pin and the structure being monitored.

26. A system for detecting defects in an object having a cylindrical surface, the system comprising:

a plurality of multiple pin electrodes sufficient to cover the circumference of the cylindrical surface, wherein each of the plurality of multi-pin electrodes comprises:

at least three current pins equally spaced from one another and being operatively connected to a current source; and at least one voltage pin, operatively connected to a voltage measurement means, and being centered relative to the current pins;

structure for operatively positioning the electrodes relative to the object and in contact with the cylindrical surface; and tension means, operatively connected to each pin, for urging the pins such that contact with the cylindrical surface is sufficiently equal between pins wherein a mathematical model can be utilized to analyze the object for defects.

* * * * *